United States Patent [19]

Grossman

[11] Patent Number: 4,667,112
[45] Date of Patent: * May 19, 1987

[54] RADIATION DISPERSING CAVITIES

[75] Inventor: Jack J. Grossman, Manhattan Beach, Calif.

[73] Assignee: McDonnell Douglas Corporation, Long Beach, Calif.

[ * ] Notice: The portion of the term of this patent subsequent to Nov. 5, 2002 has been disclaimed.

[21] Appl. No.: 740,347

[22] Filed: Jun. 3, 1985

Related U.S. Application Data

[63] Continuation-in-part of Ser. No. 481,164, Apr. 1, 1983, Pat. No. 4,551,628.

[51] Int. Cl.⁴ ............................................. B01N 21/24
[52] U.S. Cl. .................................. 250/503.1; 250/228; 356/236
[58] Field of Search ...................... 250/228, 503, 493.1; 350/613; 356/236

[56] References Cited

U.S. PATENT DOCUMENTS

| | | | |
|---|---|---|---|
| 1,888,103 | 11/1932 | Guth | 362/348 |
| 3,319,071 | 5/1967 | Worth et al. | 350/236 |
| 3,920,336 | 11/1975 | Sackett | 350/201 |
| 3,923,382 | 12/1975 | Harding | 350/613 |
| 3,972,598 | 8/1976 | Kunz | 350/613 |
| 4,195,913 | 4/1980 | Dourte et al. | 350/613 |
| 4,221,468 | 9/1980 | Macken | 350/613 |
| 4,317,042 | 2/1982 | Bartell | 250/493.1 |
| 4,514,639 | 4/1985 | Bartell | 250/493.1 |

*Primary Examiner*—Bruce C. Anderson
*Assistant Examiner*—Paul A. Guss
*Attorney, Agent, or Firm*—Gregory A. Cone; George W. Finch; Donald L. Royer

[57] ABSTRACT

A radiation dispersing cavity has its interior surface covered by a plurality of deformations, each of which acts as a dispersing element which is small with respect to the effective diameter of the cavity and yet large with respect to the wavelengths processed by the integrating cavity. The interior surface of the cavity is coated with a material which provides the proper reflectivity for the wavelengths of interest. The interior of the cavity is covered with at least two different sets of interlocking deformations producing at least two different apparent planes of reflection. Use of alternating concave-inward, concave-outward deformations facilitates smooth transitions between deformations, preventing development of hot spots at sharp discontinuities.

12 Claims, 7 Drawing Figures

RADIATION DISPERSING CAVITIES

The govenment has rights in this invention pursuant to Contract No. DASG60-79-C-0029 awarded by the Department of the Army.

This is a Continuation-In-Part of Ser. No. 481,164, filed Apr. 1,1983, now U.S. Pat. No. 4,551,628.

BACKGROUND OF THE INVENTION

This invention relates to radiation dispersing cavities. More particularly, this invention relates to radiation dispersing cavities which rely upon a large number of interlocking deformations to the surface of the cavity to achieve a very close approximation to uniform Lambertian mixing of the input radiation.

Basically, this invention has two major embodiments, one as an optical integrating cavity and one as a black body emitter. The optical integrating cavity will be discussed first. An integrating cavity can be defined as a device which mixes radiation, whether polarized or Plankian or whatever, entering the cavity from different directions and emits uniformly mixed Lambertian distributed radiation. In most of the prior art devices, the emission of the uniformly mixed radiation is along a direction orthogonal to the source or sources of radiation at the input or inputs. The homogenized radiation is then dependent upon the sum of the spectral inputs and independent of any geometrical property of the input optics.

Most integrating cavities are spherical in shape. The integrating spheres in the prior art which are used in the visible portion of the spectrum are normally made by "smoking" the inside of a spherical cavity with magnesium oxide. The magnesium oxide is transparent to visible radiation, and, in its non-absorbing spectral regime, light is partly reflected from random facets at the outer surface of the magnesium oxide coating, partly transmitted and suffers reflection and refraction at each succeeding interface which it meets. Due to the random orientation of the porous magnesium oxide smoke and its low absorption, it randomizes the directed input radiation into a random Lambertian radiation distribution. U.S. Pat. No. 4,309,746 to Rushworth illustrates the employment of the magnesium oxide internal coating for the integrating cavity in its recitation in column 5. Another common coating employed in the prior art integrating cavities is barium sulphate. Its use is demonstrated in U.S. Pat. No. 4,232,971 to Suga in its teaching at column 4. It is important to note that these prior art devices rely upon the properties of the coating material itself to randomize the reflected radiation within the integrating cavity. This should be contrasted with the fundamentally different mechanism employed in the present invention in which the conformation of the cavity surface with its interlocking deformations produces the randomizing effect through the interaction of the light in the cavity with the individual reflecting elements. Unfortunately, since these prior art devices rely upon the optical properties of the coating materials emplaced upon the interior cavity surface, the effective bandwidth of the device is limited by the properties of the internal coating. Consequently, the integrating cavity technology of the prior art has not been able to be extended satisfactorily out of the visible portion of the optical spectrum, specifically not into the infrared bandwidths with satisfactory results. One U.S. Patent in the prior art, U.S. Pat. No. 3,319,071, to Werth et al., bears further comment. This reference describes the construction of a chamber used for measuring infrared absorption characteristics of gases in which the chamber bears a superficial resemblance to one embodiment of the integrating cavity of the present invention. However, the dimples which are formed in the surface of the prior art chamber are specifically designed such that the reflections therefrom will produce specular, rather than diffuse, reflections within the sphere, as is taught at the bottom of column 2 of this reference.

SUMMARY OF THE INVENTION

The radiation dispersing cavity of this invention is for use in mixing a bandwidth of radiation and comprises a cavity surface substantially covered by a plurality of interlocking deformations, each deformation being a surface of revolution whose axis is substantially normal to the cavity surface wherein the surface of revolution is formed by a conic such that a cross section containing the axis is a portion of the conic subtending an arc of from 10° to about 140° measured from the focus of the conic and the arc has an effective diameter measured across the end points of the arc wherein the ratio of the longest wavelength in the bandwidth to the arc diameter of a deformation is less than one-fifth and wherein the diameter of the cavity is at least five times the arc diameter of a deformation, wherein the cavity surface is characterized by a specific reflectivity for the bandwidth of the radiation. The cavity itself may be, but is not limited to, a sphere, an ellipsoid, or a cylinder and is covered with a coating of proper reflectivity for operation upon the wavelengths of interest.

DETAILED DESCRIPTION OF THE INVENTION

Figure 1:
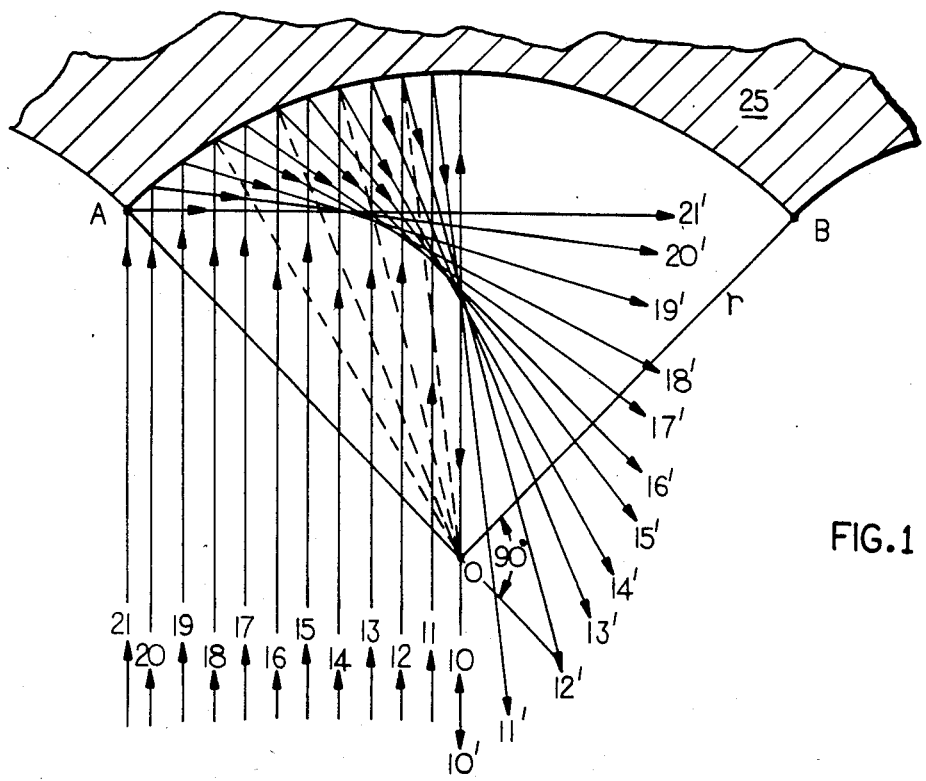
FIG. 1 is a cross-sectional view of a portion of the cavity wall with a ray diagram showing incident and reflected light rays from the reflecting element.

The physical concepts behind the radiation dispersing cavities of this invention are applicable to several different embodiments. One embodiment takes the form of integrating cavities which are useful for producing a random Lambertian radiation distribution from various input radiation sources. Another embodiment takes the form of a black body emitter which produces an electromagnetic spectral output given by Planck's radiation law which is a function only of the temperature of the black body emitter. Still another embodiment takes the form of what may be called a gray body emitter which is a combination of the above two effects for the integrating cavity and black body emitter forms of the invention. Most forms of the integrating cavity embodiment of this invention will require a high reflectivity at the reflective surface of the cavity. Normally this will be produced by a gold or gold alloy coating deposited upon the interior of the cavity. However, in some applications a silver coating or an aluminum coating may be sufficient. Additionally, if the cavity itself is fabricated from aluminum, it may be possible in some applications to dispense with the need for a coating and utilize the aluminum body material in a highly polished state directly. Although the majority of the following description will be devoted to developing those embodiments of this invention which utilize deformations which have a circular cross section, it should be realized that the cross section of these deformations is not necessarily limited to circular cross sections. In the general case, the deformations may be formed by a surface of revolution which has as its axis a line which is substantially normal to the interior surface of the dispersing cavity at the point of the deformation. This surface may be spheric or aspheric. Finally, in the way of general remarks about such dispersing cavities, the input aperture size should have an effective aperture diameter which is equal to at least the average effective diameter of the deformations inside the cavity. Also the input beam angular divergence should cover at least about five deformation diameters in order to maximize the efficiency of the dispersion chamber.

In many systems, it is desirable to take radiation from a number of different sources and combine the radiation into a prescribed spectral distribution. The spectral input can be from broad band and narrow band filtered black body sources, laser sources, spark discharge, glow discharge, and other various sources which are brought together from different directions. The integrating cavity embodiment of this invention is uniquely able to be used as a mixing chamber for these various sources of radiation and is useful over wide ranges of wavelengths, especially in the infrared region.

The integrating cavity is independent of the wavelength of the input radiation for all values of the ratio wavelength/d' for values less than about 0.20 where d' is the diameter of the deformation in the surface of the integrating cavity. While d' is the effective diameter of the circular deformation measured at the surface, it should be remembered that d is a separate dimension which is equal to twice the radius of curvature of the circular cross-section deformation. Concurrently, the effective diameter of the cavity must be greater than about five times the diameter of the deformations. When both of these conditions are satisfied, the bandwidth of the integrating cavities is limited only by the absorption properties of the specularly reflective film used to coat the interior of the cavity.

Up to this point, the integrating cavities of this invention have been discussed in general terms. Specific configurations of the cavity include spheres, ellipsoids, and cylindrical cavities. The following discussion will concentrate first on the integrating sphere.

The theory of operation for the integrating sphere embodiment, although the theory holds true for the other embodiments as well, is that if the inside of a sphere having a radius, R, is covered with spherical concave or convex deformations where the radius of curvature, r, is small compared to the radius of the integrating sphere, then each lens-like surface can transform an incident plane wave of light into a divergent wave front filling almost 2 steradians. This effect is shown in FIG. 1, which portrays a cross-sectional view of the interior of the integrating sphere showing the sphere wall 25 in cross section and the circular arc AB which is the cross-sectional view of one of the spherical deformations in the integrating sphere. Point O is the center of curvature for the spherical deformation having a radius r. In this particular embodiment, the arc subtends an angle of 90° which for most purposes will be desirable since it will minimize the surface area of the integrating cavity while maximizing the solid angle into which the plane wave is reflected. FIG. 1 shows an incident plane wave front which bisects the angle AOB. Since the angle AOB is a right angle, the rays 10 thru 21 will be reflected as shown from the arcuate surface of the reflecting element into the reflected rays 10' through 21', with ray 10 being reflected back upon itself and ray 21 being reflected as a right angle and with the other rays reflecting at angles distributed uniformly between these two extremes. Similar geometric constructions for plane waves incident at both small and large angles demonstrate that the reflected wave fronts will spread over large solid angles approaching $2\pi$ steradians. Such constructions of plane wave normals incident at increasing angles to ray 10 show that the caustics of reflected ray bundles translate towards the periphery of each indentation. Since the incident waves come from all directions, the reflected rays which exit from the output aperture will appear to emanate approximately uniformly from all areas of each indentation.

A common objective for the use of an integrating cavity is to transform broad band radiation directed into the input aperture of the cavity into non-directional radiation exiting through the output aperture. To achieve this, normally the integrating cavity must randomize the radiation so that it is unpolarized, and the flux density inside the cavity must be uniform in all directions. When this condition is met, the directional intensity of radiation which exits the aperture is distributed according to the Lambertian $\cos^2 \theta$ law. Interestingly, since the construction of the present invention so effectively scatters the incident light, there is no significant direct reflection from the opposite wall back through the inlet aperture, and hence no strict requirement for a non-diametrical viewing direction or exit aperture as is found in the prior art of integrating cavities.

Figure 2:
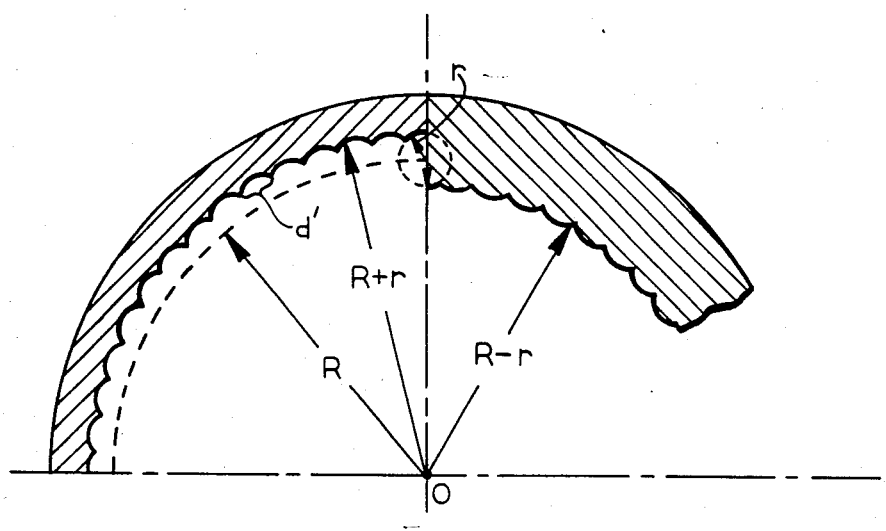
FIG. 2 is a cross-sectional view of two larger portions of cavity walls showing in the left quadrant an embodiment with the reflecting elements being concave inward and in the right quadrant showing reflecting elements which are convex inward.

The integrating sphere of this embodiment accomplishes this randomization by dividing the interior surface of the integrating sphere into a large number of short focal length spherical mirrors which are spaced such that no extended area of the original spherical surface of the sphere remains. Only sharp edges and points at the intersections of these spherical mirrors exist in addition to the short focal length curved surfaces themselves, and these should have smaller convex radii of curvature than the shortest wavelengths of interest. FIG. 2 shows two different configurations for the spherical deformations in the integrating sphere. In the left quadrant, the short focal length curved surfaces are convex inwards. The center of the integrating sphere is shown as point O, the cross-sectional view exposes the material in the integrating sphere wall 25, the effective radius of the integrating sphere is R, and the distances to the centers of the arcs of the respective elements are R+r and R−r, respectively. Again, the radius of curvature of the individual spherical deformations is r. It is anticipated that the concave inwards embodiment would be easier to fabricate; however, either implementation is effective.

Figure 3:
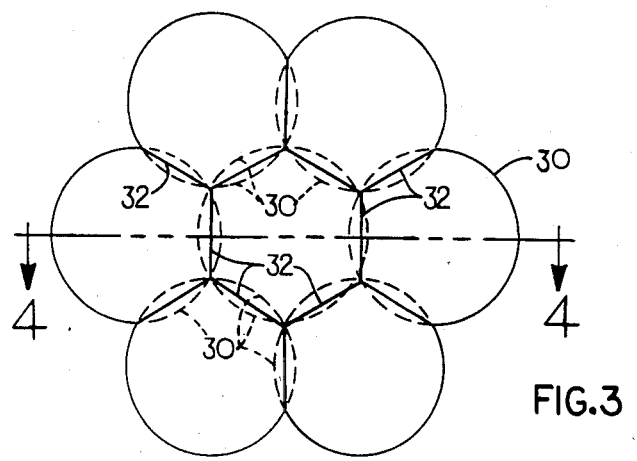
FIG. 3 is a plan view of a portion of the cavity wall for an embodiment for which the reflecting elements are spherical indentations.

FIG. 3 shows in plan view the interlocking spherical deformations in the wall of the integrating cavity. The perimeters of each of the deformations as they would intersect the original interior surface of the cavity are shown as the dotted lines 30. However, since they interlock, the actual boundaries between the elements will be marked by the straight line segments 32 which form a honeycomb-like pattern of interlocking hexagons on the surface of the cavity. Note that the discussion above requires that these straight line segments 32 and their respective intersections all have radii of curvature which are smaller than the wavelengths of interest for the integrating cavity.

Figure 4:
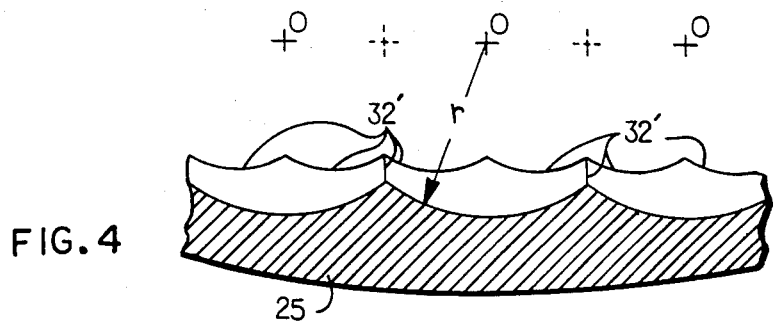
FIG. 4 is a cross-sectional view taken along section lines as indicated in FIG. 3.

FIG. 4 shows a cross-sectional view of the plan view shown in FIG. 3. The cavity wall material 25 is shown in cross section along with the corresponding arcuate segments 32' which correspond to the straight line segments 32 in FIG. 3. The centers of curvature for the individual deformations are shown as the crosses labelled O. Corresponding centers of curvatures for the elements which are out of the plane of section are shown by the dotted crosses. This discussion has assumed that the spherical deformations are all essentially identical in size. This is not a requirement for the operability of the device. The only requirement is that the diameter of the spherical elements as they deform the surface is large with respect to the wavelengths involved. Hence, there could be two or more different sizes of deformations in the wall of the integrating cavity. For example, the points of intersection of the arcuate lines 32 in FIG. 3 could serve as centers for a second set of deformations having a smaller effective diameter than the original deformations 30. Nevertheless, regardless of the size of the deformations, they must interlock in arcuate lines and/or at points of intersection.

Figure 3A:
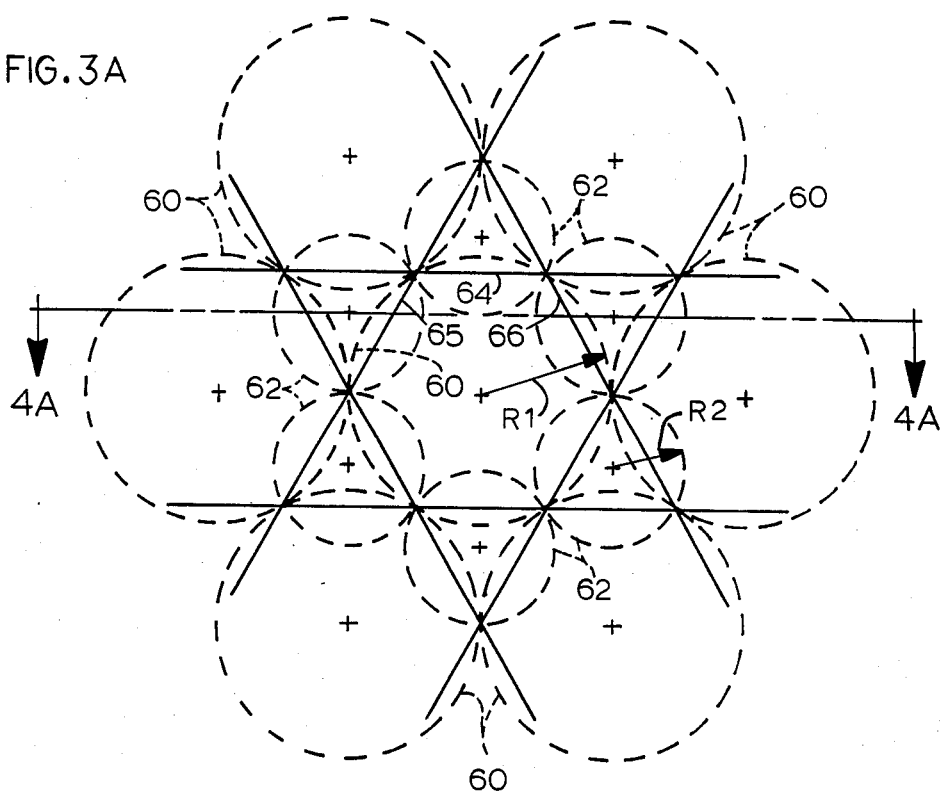
FIG. 3A is a plan view of a portion of the cavity wall for an embodiment having two different sets of spherical deformations.
Figure 4A:
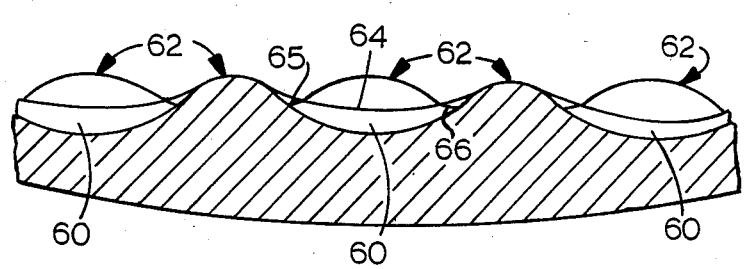
FIG. 4A is a cross-sectional view taken along section lines as indicated in FIG. 3A showing alternating hills and valleys for the deformations.

Alternate embodiments of the concept introduced immediately above are shown in FIGS. 3A and 4A. The basic concept of utilizing different sizes of deformations, although somewhat more difficult to fabricate, permits the utilization of multiple apparent planes of reflection. For the purposes of this discussion, an apparent plane of reflection is that plane which contains the average depth points for a given set of deformation elements. The average depth point for a deformation is defined herein as the midpoint between the most distal point in a deformation and the most proximate point, both relative to the center of the cavity, the midpoint being located on the axis of the surface of revolution which defines the deformation. Multiple apparent planes of reflection in turn create more dispersion than would a single apparent plane of reflection and result in a dispersion of radiation that more closely approaches that of the ideal $\cos^2 \theta$ distribution. The use of two different sizes of deformations is shown in plan view in FIG. 3A. Whereas the embodiment shown in FIG. 3 produces an interlocking hexagonal intersection grid, the grid in FIG. 3A is made up of interlocking hexagons and equilateral triangles as shown. These hexagons correspond, for the specific embodiment shown, to the concave inwards larger radius ($r_1$) deformations 60 (valleys) shown in the cross section view taken along section line 4A—4A shown in FIG. 4A. The triangles correspond to the tighter radius ($r_2$) convex inwards deformations 62 (hills) also shown in FIG. 4A. This specific embodiment produces two separate apparent planes of reflection, one from the hills and one from the valleys. Addition of further sets of interlocking elements in a similar fashion will produce additional apparent planes of reflection. FIGS. 3A and 4A also illustrate the concept of alternating interlocking hills and valleys in constructing the deformations. This concept is desirable in that it produces relatively smoother transitions (64, 65 and 66 in FIGS. 3A and 3B) at the interlocking intersections between deformations as opposed to the relatively sharp ridges produced when only valleys are used for deformations or the acute valleys formed at the intersections between the hills-only construction, these effects being illustrated respectively in the left and right quadrants of FIG. 2.

One method of fabrication for the integrating sphere embodiment is to machine a master integrating sphere on the inside surface of a spherical cavity cut into several sections. The individual deformations would then be machined into the surface with continuity maintained across mating edges of the various sections of the sphere. Next, a silicone rubber or other flexible plastic mold which can be electrically conductive or non-conductive is made of each half of the sphere. These negative molds are then used for electroless and/or electrolytic plating of a large number of substantially identical integrating spheres. First a reflective or absorbing coating such as gold is deposited and then a base structural metal such as copper is deposited until the wall thickness produces a mechanically stable structure. Another method would be to use a solid form which is divided into eight equilateral spherical right triangles as the plating mold sections. When finished, the mold would slip out of the plated part without interference.

For general example, consider a one centimeter diameter integrating sphere with surface area of $4\pi R^2 = \pi \text{cm}^2$. If an individual scattering element has an equivalent projected area of a one millimeter diameter plane circle, then the area of each element would be $\pi r^2 = \pi/4 \text{ mm}^2$. Therefore, the inside of the sphere would contain about 400 such elements. For the infrared five to 25 micron band, the ratio of the diameter of the element to the wavelength varies from 40 at 25 microns to 200 at five microns. For these dimensions, the size of the spherical reflecting elements will not contribute appreciably to wavelength dependent phenomena. This should be contrasted to the prior art devices which normally employ SiC scattering centers deposited on the inside surface of the integrating cavity which are then overplated with a suitable high reflectivity material such as gold. In these prior art devices, the scattering centers cannot be well controlled and give rise to these detrimental wavelength dependent phenomena.

In another example, a 50 millimeter diameter integrating sphere is covered with 3 millimeter diameter spherical reflecting elements to cover the infrared band from five microns to 30 microns. The ratio of the element diameter to the largest wavelength (d/wavelength=100) shows that no spectral effects should be observed. Performing a computation based on the hexagonal geometry shown in FIG. 3, the number of reflecting elements possible is given by $$N = \text{Area}_{sphere}/\text{Area}_{hexagon} = (4\pi R^2) \div \left(\frac{3\sqrt{3}}{2} r^2\right)$$

$$= 1340 \text{ elements}$$

For these dimensions, each reflecting element occupies a solid angle of about $9.4 \times 10^{-3}$ sr (or 1.57° full cone angle) measured from the exit port of the integrating sphere. Since the number of reflecting elements increases inversely as the square of the radius, the number of elements could be increased by a factor of 10 and still allow for ten wavelengths across each element for radiation at 30 microns.

Figure 5:
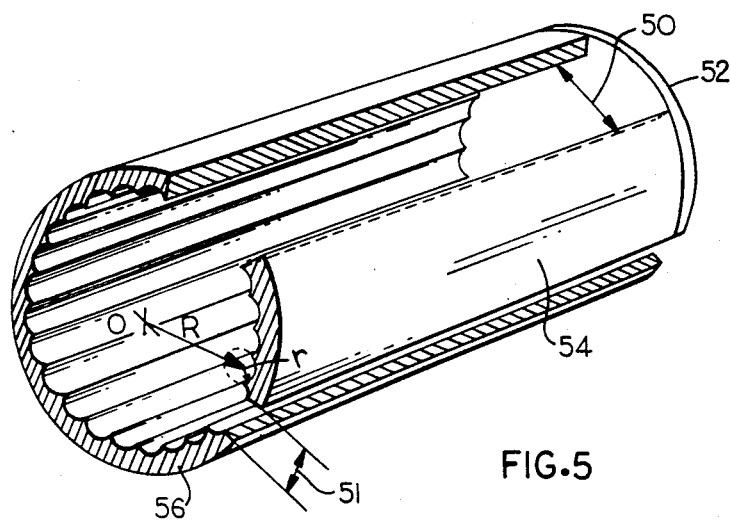
FIG. 5 is an isometric view of another embodiment of the invention in which the integrating cavity is in the form of a cylinder with its reflecting elements being parallel cylindrical arcs incised into the cavity surface.

A second embodiment of this invention is a cylindrical integrating cavity. Such cylindrical integrating cavities are useful in mixing radiation input into the cavity from a line source. One such cavity is shown in FIG. 5. The cylindrical cavity shell 54 is pierced by an entrance slit parallel to its long axis having an opening width marked by the numeral 50. A corresponding exit slit has its opening width labelled 51. However, it should be noted that the high efficiency dispersion characteristic of the interior surface does not necessarily require separate entrance and exit slits; a single slit could suffice for some usages. The cylinder is capped at each end by mirror end caps 52, one of which has been removed to show the detailed construction of the interior of the cavity. In one version of this embodiment, the individual reflecting elements take the form of cylindrical grooves incised into the cylinder walls, each of which has an individual radius of curvature marked r. The radius of the cylindrical integrating cavity itself is R which represents the radius of the interior of the cavity prior to the formation of the individual cylindrical reflecting grooves. As before, these grooves need not be concave inwards as shown in this figure, but could be alternatively formed as convex inward lands. In another alternative, the grooves and lands can alternate. The axial center of the integrating cylinder is marked by the centerpoint labelled O. This particular version of the cylindrical integrating cavity is useful in its employment in a larger system which comprises a single line source coupled to the cylindrical integrating cavity by a waveguide in which it is desirable for the polarization of the waveguide polarized radiation to be preserved. The waveguides coupling the single line source and the integrating cavity produce polarized radiation with the electric vector perpendicular to the plane faces of the waveguide. The employment of the long cylindrical grooves cut in the cylindrical integrating cavity preserve the polarization of this radiation. Nevertheless, in situations where it is not necessary to preserve this polarization, the spherical dimple version discussed in relationship to the spherical integrating cavity above may be employed in the interior of the cylindrical integrating cavity. This particular version is not shown.

Returning to a more general discussion, the integrating cavity is constructed in accordance with this invention may be used in the ultraviolet, visible, the near infrared, the far infrared, sub millimeter and millimeter bands of electromagnetic spectrum to transform directional light sources of any spectral bandwidth into a path or history independent Lambertian output beam which is directly proportional to the total energy in the beam. Similarly it can mix a number of different spectral sources (broadband, band-limited and monochromatic in any combination) into a new source in which the output spectrum has a predetermined (preset) distribution. Also the integrating cavity may act as a near neutral density beam attenuating component by selection of a suitable coating material for the interior of the integrating cavity with an appropriate reflectivity coefficient to produce the desired attenuation.

As was stated above, the optimum arc for the individual reflecting elements to subtend is approximately 90° measured from the center of curvature of the arc. However, it is possible that this arc may fall anywhere in the range from about 10° at the minimum to about 140° at the maximum before inefficiencies overcome the construction. At the low end (10°) the deformation becomes so shallow that the dispersing characteristic of the reflectivity of the surface becomes too small and direct reflections or glance begin to domonate. At the high end of the range (140°) internal reflections within each reflecting element introduce inefficiencies due to absorption effects from these multiple reflections from the coating material. Also, in some situations it may be desirable to use an arc which is slightly less than 90° in situations in which heat transfer effects at the sharp edges and ridges between the elements become important. These usages include measurements conducted in the infrared regions.

Another significant usage for the radiation dispersing cavity of this invention is in black body emitters. These devices are used to produce an electromagnetic spectral output given by Planck's radiation law which is a function only of temperature. The only significant physical difference between the optical integrating cavities discussed above and the black body emitter is in the reflectivity of the interior surface or the surface coating of the chamber. In the case of the integrating cavities, the reflectivity of the coating will normally be very high, although in some instances the integrating cavity may be employed either as a neutral density or spectral filter and will have a lower reflectivity coating in order to partially attenuate the radiation as it reflects off the interior surfaces of the chamber. However, the black body emitter depends for its functioning upon a very low reflectivity surface or surface coating, since the object is to have a very high absorption at the chamber surface rather than high reflectivity as is the case in the integrating cavities except that the black body cavity is heated to some controlled temperature and the integrating cavity is cooled to prevent it from adding energy into the spectral band of interest. The actual geometric construction of the black body emitter is substantially identical to the construction of the various embodiments of the integrating cavities. In both the object is to have optimal diffusion of the reflected component of the cavity radiation from the multiple interlocking reflecting elements formed in the wall of the chamber. The output radiation from the cavity is then sampled or utilized after it leaves the cavity via the output aperture. Hence, although the most common embodiment for the black body emitter will be the spherical chamber with spherical deformations forming the interlocking reflecting elements on its interior, it is possible that cylindrical and elliptical black body emitter chambers may also be utilized should the specific application so require.

Another embodiment is a hybrid radiation dispersing cavity which may be called a modified grey-body source which generates part of its energy thermally and obtains part from another radiation source which feeds into it.

I claim:

1. A cavity for the diffusion of radiation of a bandwidth having a maximum wavelength of about 100 microns comprising a cavity surface substantially covered by a plurality of interlocking deformations comprising at least two sets of deformations for producing at least two apparent planes or reflection from at least two different sets of deformations wherein adjacent deformations have opposite concavities such that no sharp intersections between deformations are present, each deformation being a surface of revolution whose axis is substantially normal to the cavity surface wherein the surface of revolution is formed by a conic such that a cross section containing the axis is a portion of the conic subtending of arc of from 10° to about 140° measured from the focus of the conic and the arc having an effective diameter measured across the end points of the arc wherein the ratio of the longest wavelength in the bandawidth to the arc diameter of a deformation is less than one-fifth and wherein the diameter of the cavity is at least five times the arc diameter of a deformation, wherein the cavity surface is characterized by a specific reflectivity for the bandwidth of the radiation wherein the cavity comprises an enclosed surface having at least one aperture to serve as inlet and outlet apertures such that a Lambertian distribution of radiation is produced and is accessible at the outlet aperture.

2. A cavity for the diffusion of radiation of a bandwidth having a maximum wavelength of about 100 microns comprising a cavity surface substantially covered by a plurality of interlocking deformations comprising at least two sets of deformations for producing at least two apparent planes of reflection from at least two different sets of deformations wherein adjacent deformations have opposite concavities such that no sharp intersections between deformations are present, each deformation having a cross section which is a portion of a circle subtending an arc of from about 10° to about 140° measured from the center of curvature of the deformation and the arc having a diameter measured across the end points of the arc wherein the ratio of the longest wavelength in the bandwidth to the arc diameter of a deformation is less than one fifth and wherein the diameter of the cavity is at least five times the arc diameter of a deformation, wherein the cavity surface is characterized by a specific reflectivity for the bandwidth of the radiation wherein the cavity comprises an enclosed surface having at least one aperture to serve as inlet and outlet apertures such that a Lambertian distribution of radiation is produced and is accessible at the outlet aperture.

3. The radiation diffusion of claim 2 wherein the cavity is an integrating cavity.

4. The radiation diffusion cavity of claim 2 wherein the cavity is to be used as a black body emitter through the aperture wherein the reflectivity of the surface is less than about 1.0%.

5. An integrating cavity for mixing radiation of a bandwidth having a maximum wavelength of about 100 microns comprising a cavity surface substantially covered by a plurality of interlocking deformations comprising at least two sets of deformations for producing at least two apparent planes of reflection from at least two different sets of deformations wherein adjacent deformations have opposite concavities such that no sharp intersectons between deformations are present, each deformation having a cross section which is a portion of a circle subtending an arc of from about 10° to about 140° measured from the center of curvature of the deformation and a diameter measured across the end points of the arc wherein the ratio of the longest wavelength in the bandwidth to the diameter of a deformation is less than one tenth and wherein the diameter of the cavity is at least five times the diameter of a deformation, wherein the cavity surface is covered with a coating of a specific reflectivity for the bandwidth of the radiation wherein the cavity comprises an enclosed surface having at least one aperture to serve as inlet and outlet apertures such that a Lambertian distribution of radiation is produced and is accessible at the outlet aperture.

6. The integrating cavity of claim 5 wherein the cavity is a spherical cavity.

7. The integrating cavity of claim 6 wherein the deformations are spherical deformations.

8. A spherical integrating cavity for dispersing radiation of a bandwidth having a maximum wavelength of about 100 microns comprising a cavity surface substantially covered by a plurality of interlocking deformations comprising at least two sets of deformations for producing at least two apparent planes of reflection from at least two different sets of deformations, wherein adjacent deformations have opposite concavities such that no sharp intersections between deformations are present, each deformation having a cross section which is a portion of circle subtending an arc of from about 10° to about 140° measured from the center of curvature of the deformation and a diameter measured across the end points of the arc wherein the ratio of the longest wavelength in the bandwidth to the diameter of a deformation is less than ten and wherein the diameter of the cavity is at least five times the diameter of a deformation, wherein the cavity surface is covered with a coating of a specific reflectivity for the bandwidth of the radiation wherein the cavity comprises an enclosed surface having at least one aperture to serve as inlet and outlet apertures such that a Lambertian distribution of radiation is produced and is accessible at the outlet aperture.

9. The cavity of claim 8 wherein the deformations are spherical deformations.

10. The cavity of claim 9 wherein the deformations are configured as two sets of interlocking deformations, the first set consisting of concave inwards deformations having a first apparent plane of reflection and the second set consisting of convex inwards deformations having a second apparent plane of reflection.

11. The cavity of claim 9 wherein the deformations are configured as at least two sets of interlocking deformations, at least one set consisting of concave inwards deformations having a first apparent plane of reflection and at least one remaining set consisting of convex inwards deformations having a second apparent plane of reflection.

12. The cavity ofclaim 8 wherein the arc is from about 70° to about 100°.

* * * * *